United States Patent
Ozawa et al.

(10) Patent No.: US 9,453,255 B2
(45) Date of Patent: Sep. 27, 2016

(54) SAMPLE ANALYSIS CHIP, SAMPLE ANALYSIS METHOD AND GENE ANALYSIS METHOD

(71) Applicant: TOPPAN PRINTING CO., LTD., Tokyo (JP)

(72) Inventors: Tomoyuki Ozawa, Kitakatsushika-gun (JP); Tomoko Kishimoto, Kitakatsushika-gun (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 13 days.

(21) Appl. No.: 14/283,561

(22) Filed: May 21, 2014

(65) Prior Publication Data

US 2014/0255933 A1    Sep. 11, 2014

Related U.S. Application Data

(63) Continuation of application No. PCT/JP2012/080273, filed on Nov. 22, 2012.

(30) Foreign Application Priority Data

Nov. 25, 2011 (JP) ................. 2011-257824

(51) Int. Cl.
| | |
|---|---|
| C12M 1/00 | (2006.01) |
| C12Q 1/68 | (2006.01) |
| C12M 1/34 | (2006.01) |
| C12M 3/00 | (2006.01) |
| G01N 15/06 | (2006.01) |
| G01N 33/00 | (2006.01) |
| G01N 33/48 | (2006.01) |
| G01N 35/00 | (2006.01) |
| B01L 3/00 | (2006.01) |
| B01L 7/00 | (2006.01) |

(52) U.S. Cl.
CPC ............. *C12Q 1/68* (2013.01); *B01L 3/50273* (2013.01); *G01N 35/00069* (2013.01); *B01L 3/502707* (2013.01); *B01L 7/52* (2013.01); *B01L 2200/025* (2013.01); *B01L 2200/0673* (2013.01); *B01L 2200/0684* (2013.01); *B01L 2200/0689* (2013.01); *B01L 2200/16* (2013.01); *B01L 2300/0803* (2013.01); *B01L 2300/0864* (2013.01); *B01L 2400/0409* (2013.01)

(58) Field of Classification Search
CPC ............ C12Q 1/68; C12M 1/34; B01L 3/50; G01N 33/48
USPC .................... 435/6.1, 283.1, 288.5; 422/68.1
See application file for complete search history.

(56) References Cited

U.S. PATENT DOCUMENTS

| | | | | |
|---|---|---|---|---|
| 8,546,129 | B2* | 10/2013 | Ozawa | B01L 3/50273 422/68.1 |
| 2002/0047003 | A1* | 4/2002 | Bedingham | B01L 3/5025 219/388 |
| 2006/0252144 | A1* | 11/2006 | Sandell | B01F 13/0059 435/288.5 |
| 2010/0081213 | A1 | 4/2010 | Lee et al. | |
| 2011/0189701 | A1* | 8/2011 | Kim | B01L 3/50273 435/7.9 |
| 2012/0184025 | A1* | 7/2012 | Kawata | G01N 21/07 435/287.2 |

FOREIGN PATENT DOCUMENTS

| | | |
|---|---|---|
| CN | 101971035 | 2/2011 |
| JP | 2004-502164 | 1/2004 |
| JP | 3699721 | 9/2005 |
| JP | 2008-083017 | 4/2008 |
| JP | 2011-196849 | 10/2011 |
| WO | WO 02/01180 A2 | 1/2002 |
| WO | WO 02/074438 A2 | 9/2002 |
| WO | WO 2006/006591 A1 | 1/2006 |
| WO | WO 2010/113959 A1 | 10/2010 |
| WO | WO 2011/040504 A1 | 4/2011 |

OTHER PUBLICATIONS

JP 2001-196849—Description, Machine translation, pp. 1-12, printed on Jan. 15, 2016.*
JP 2001-196849—Drawing, pp. 1-11, printed on Jan. 15, 2016.*
JP 2001-196849—Drawing Description, Machine translation, pp. 1-2, printed on Jan. 15, 2016.*
Extended European Search Report dated Jun. 15, 2015 in corresponding European Patent Application No. 12851905.5.
Chinese Office Action issued Dec. 5, 2014 in corresponding Chinese Patent Application No. 201280057620.8.
International Search Report mailed Feb. 5, 2013 in corresponding International Application No. PCT/JP2012/080273.

* cited by examiner

*Primary Examiner* — Narayan Bhat

(57) ABSTRACT

A sample analysis chip of the present invention includes a base, a plurality of wells that are disposed on the base, a main channel, a first buffer portion that is in communication with a first end of the main channel and is capable of accommodating a portion of the solution, a second buffer portion that is in communication with a second end of the main channel and is capable of accommodating a portion of the solution, a solution supply channel a first end of which is in communication with the first buffer portion and a second end of which is opened to the atmosphere, an air vent channel a first end of which is in communication with the second buffer portion and a second end of which is opened to the atmosphere, and the channel that is disposed on the base and connected to the plurality of wells.

25 Claims, 11 Drawing Sheets

SAMPLE ANALYSIS CHIP, SAMPLE ANALYSIS METHOD AND GENE ANALYSIS METHOD

CROSS REFERENCE TO RELATED APPLICATIONS

This application is a continuation application based on a PCT Patent Application No. PCT/JP2012/080273, filed Nov. 22, 2012, whose priority is claimed on Japanese Patent Application No. 2011-257824 filed on Nov. 25, 2011, the contents of which are hereby incorporated by reference in their entirety.

BACKGROUND OF THE INVENTION

1. Field of the Invention

The present invention relates to a sample analysis chip, a sample analysis method, and a gene analysis method.

2. Description of the Related Art

Conventionally, in the field of biochemical reactions such as a DNA reaction and a protein reaction, techniques using reaction devices called Total Analysis System (μ-TAS) and Lab-on-Chip that process a minute amount of sample solution are known. These devices consist of a single chip or cartridge provided with a plurality of reaction chambers (hereinafter, referred to as "wells") or channels and make it possible to analyze a plurality of specimens or perform a plurality of reactions. It is known that in the aforementioned technique, the amount of chemicals to be handled can be reduced by miniaturizing the chip or cartridge, and accordingly, the technique has a variety of advantages.

The technique has, for example, the following merits. Since a strong acid or a strong alkali that has been conventionally used is used in a minute amount in this technique, the influence on the human body or the environment is significantly minimized. Moreover, since expensive reagents, which are used in biochemical reactions and the like, are consumed in a minute amount in this technique, the costs for analysis or reaction can be reduced.

In order to most efficiently perform a biochemical reaction by using the chip or cartridge, different kinds of chemicals, specimens, or enzymes need to be respectively allocated in a plurality of wells, and reagents for performing reactions with these chemicals, specimens, and enzymes need to flow into wells at once from a singularity or plurality of main conduits so as to perform a plurality of different reactions.

If such a technique is used, it is possible to simultaneously process a plurality of kinds of specimens with the same reagent, or, inversely, it is possible to simultaneously perform a plurality of processes on one kind of specimen. Accordingly, it is possible to greatly reduce the time and effort required and to greatly reduce the cost.

In using this type of technique, a technique of providing a sample solution to a plurality of reaction fields in the same amount and a technique of preventing the contents of the respective wells from being mixed with one another become important. Examples of prior art relating to such a chip used to providing the solution to wells include the following.

Published Japanese Translation No. 2004-502164 of the PCT International Publication (hereinafter, PTL 1) discloses a chip used to provide the solution to wells from solution reservoirs by using a centrifugal force, in which channels are deformed and sealed to separate the wells from one another.

In Japanese Patent No. 3699721(hereinafter, PTL 2), rotation and revolution are combined with each other for centrifugation so as to resolve the variation in the amount of the solution provided to each well.

Japanese Unexamined Patent Application, First Publication No. 2008-83017 (hereinafter, PTL 3) discloses an analysis medium in which a plurality of solution reservoir parts is connected to a plurality of wells having channels extending in centrifugal direction. However, this document does not focus on dispensing properties of the solution or the like. Inversely, the document describes the control of a fluid by using a phenomenon in which the fluid and air which are confined in a well push against each other.

However, the chip disclosed in PTL 1 requires a mechanism for crushing the channels, and it is difficult to automate. Moreover, if a solution is centrifugally provided from the central solution reservoir to the peripheral wells as in the conventional centrifugal solution-providing chip, the amount of solution provided to each well varies.

Furthermore, in order to adopt the centrifugal method disclosed in PTL 2, a complicated mechanism, which is used to cause the chip to make a rotation and a revolution, and a space are necessary.

In addition, with the analysis medium disclosed in PTL 3, the solution in a channel between the solution reservoir parts is not provided, and the amount of solution provided to each well shows considerable variation. Accordingly, the results obtained from each reaction show variation.

SUMMARY OF THE INVENTION

The present invention has been made in consideration of the above circumstances, and an object thereof is to provide a low-cost sample analysis chip in which a solution is provided by a simple method, the amount of the solution in each well shows a small degree of variation, and a chemical reaction and an enzyme reaction performed by heating and cooling, or warming can be suitably conducted.

In order to achieve the above object, the present invention proposes the following means.

A sample analysis chip according to a first aspect of the present invention includes a base, a plurality of wells that is disposed on the base, a main channel that is disposed at a position closer to the rotation center than to the plurality of wells on the base and is supplied with a solution which is to be dispensed to each of the plurality of wells, a first buffer portion that is in communication with a first end of the main channel and is capable of accommodating a portion of the solution, a second buffer portion that is in communication with a second end of the main channel and is capable of accommodating a portion of the solution, a solution supply channel a first end of which is in communication with the first buffer portion and a second end of which is opened to the atmosphere, an air vent channel a first end of which is in communication with the second buffer portion and a second end of which is opened to the atmosphere, and a channel that is disposed on the base and is connected to the plurality of wells. In the sample analysis chip, the base rotates on the rotation center, whereby the solution in the main channel moves into the wells.

It is preferable that the channel be formed in a groove shape on the base. Moreover, it is preferable that the sample analysis chip further includes a sealing member that is fixed to the base and sealing the channel.

Moreover, it is preferable that both of the second end of the solution supply channel and the second end of the air vent channel be opened to the atmosphere on the surface which is opposite to the surface on which the channel is formed.

Further, it is preferable that a cross-section area orthogonal to a flow direction of the solution in the second buffer portion be greater than a cross-section area orthogonal to a flow direction of the solution in the main channel.

In addition, it is preferable that a volume of the second buffer portion be greater than a volume of the main channel.

Moreover, it is preferable that the volume of the second buffer portion be greater than a volume of the first buffer portion, and a total volume of the first buffer portion and the volume of the second buffer portion is greater than the volume of the main channel.

It is preferable that the sample analysis chip include a lip portion that is formed in a wall shape that surrounds the second end of the solution supply channel and the second end of the air vent channel, is deformed by a device or a jig which is used to block the second end of the solution supply channel and the second end of the air vent channel, after the solution is injected into the channel, and the lip portion thereby being capable of keeping the channel sealed.

It is preferable that the main channel have ridges positioned near the rotation center of the base and valleys positioned near the wells relative to the ridges, the main channel be formed to meander. Moreover, it is preferable that the wells be in communication with the valleys.

Furthermore, it is preferable that the channel width of the main channel be relatively small in the ridges and be relatively great in the valleys.

In addition, a first side of the ridge and a second side of the ridge that interpose the peak of the ridge therebetween may be asymmetric.

It is preferable that the base be discoid. Moreover, it is preferable that the plurality of wells be disposed on a concentric circle with the base.

It is also preferable that the sample analysis chip have a plurality of side channels that communicate the main channel to the plurality of channels.

Moreover, it is preferable that in the sample analysis chip of the present invention, a support portion which is for rotating the base to provide the solution by a centrifugal force be disposed on the base. Further, it is preferable that the support portion be placed at the outer circumferential portion of the base.

In addition, a position detection structure which is for detecting a position and an angle of each well before and after a centrifugation process performed by using the rotation center as a center is disposed on the base. It is preferable that the position detection structure have a mechanical-detected portion that consists of a notch, a hole, or a bump. Moreover, it is preferable that the position detection structure have an optical-detected portion. It is also preferable that the surface roughness or optical characteristics of the optical-detected portion be different from the surface roughness or optical characteristics of sites of the base, at which the optical-detected portion is not provided.

It is preferable that each of the plurality of side channels be formed to become oblique to a straight line that connects the well which is connected to the side channel among the plurality of wells, to the rotation center of the base.

Moreover, the main channel may be formed so as to become oblique to the direction of the rotation center.

It is also preferable that the sample analysis chip have a first base on which the plurality of wells and the channel is formed and a second base which is bonded to the first base.

Further, it is preferable that at least one of the first base and the second base be formed of an optically transparent material.

In addition, it is preferable that the first base be formed of an optically transparent resin material, and the second base be formed of a metallic material.

A sample analysis method according to a second aspect of the present invention, using the sample analysis chip of the present invention, includes a step of injecting the solution into the main channel, and a step of dispensing the solution to each of the wells by rotating the base.

Moreover, it is preferable that the sample analysis method include a step of dispensing a mineral oil to each of the wells after the step of dispensing the solution to the wells.

A gene analysis method according to a third aspect of the present invention uses the sample analysis method of the present invention.

Advantageous Effects of Invention

According to the sample analysis chip of the first aspect of the present invention, a solution is provided by a simple method, the amount of the solution in each well shows a small degree of variation, and a chemical reaction and an enzyme reaction can be suitably performed by heating and cooling or warming. Accordingly, cost reduction can be realized.

Moreover, according to the sample analysis method of the second aspect of the present invention, and the gene analysis method of the third aspect of the present invention, a sample can be analyzed with a high degree of accuracy and reproducibility.

DETAILED DESCRIPTION OF THE INVENTION

Figure 1:
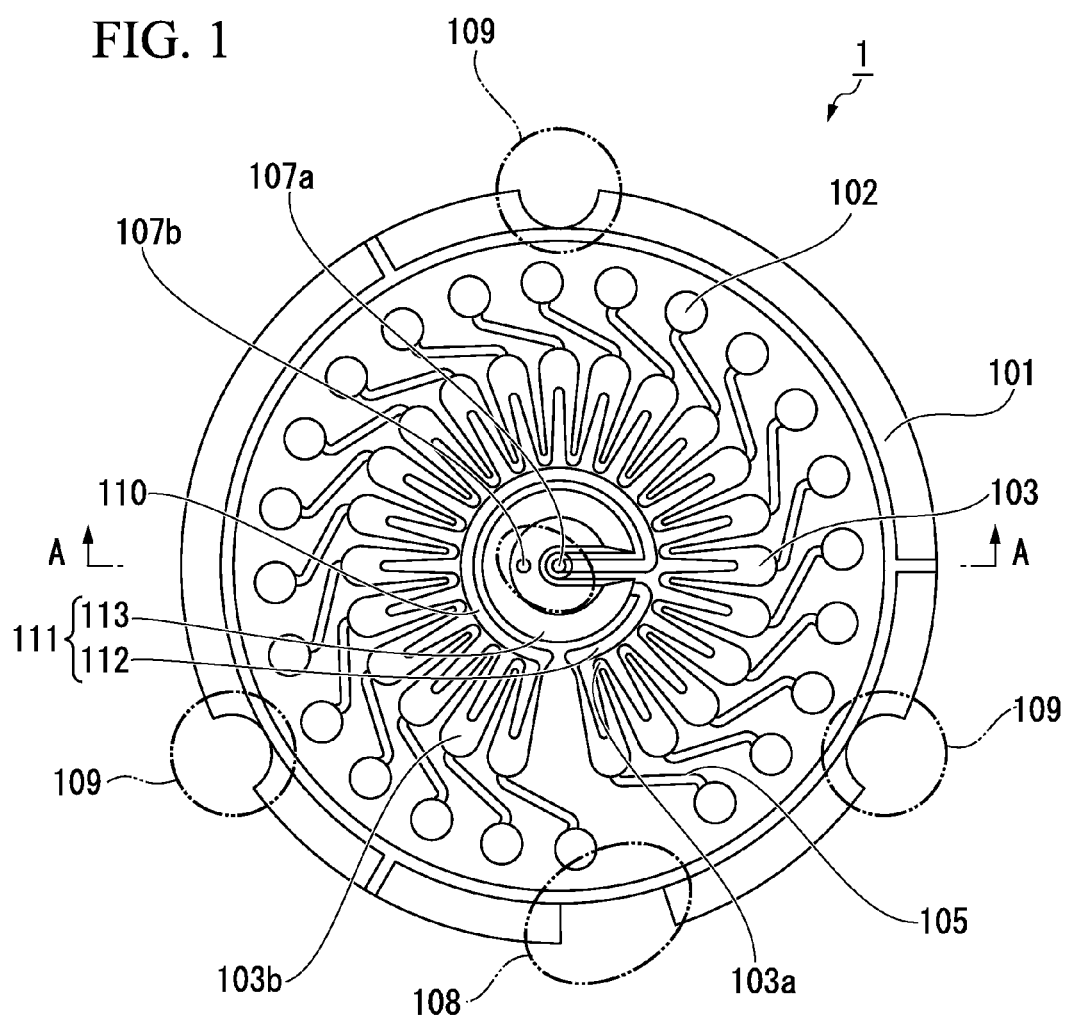
FIG. 1 is a plan view showing a sample analysis chip according to a first embodiment of the present invention.
Figure 2:
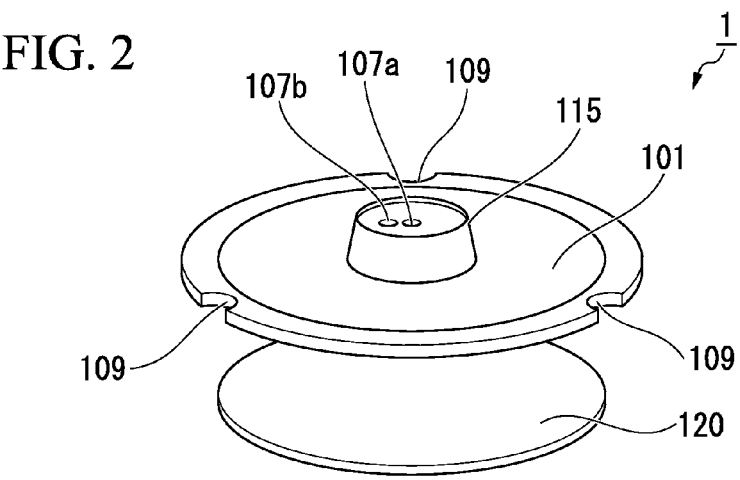
FIG. 2 is an exploded perspective view of the aforementioned sample analysis chip.

A sample analysis chip according to an embodiment of the present invention will be described based on drawings. FIG. 1 is a plan view showing an aspect of the sample analysis chip of the present embodiment. FIG. 2 is an exploded perspective view showing an aspect of the structure of the sample analysis chip of an aspect of the present embodiment.

As shown in FIG. 1, a sample analysis chip 1 has a base 101, a second base 120, a plurality of wells 102 disposed on the base 101, and a channel (consisting of a main channel 103 and side channels 105) used to provide a solution to the wells 102.

The sample analysis chip 1 is in the form of a disk as a whole and is rotated on the central point of the disk as a rotation center by an analysis device or the like not shown in the drawing. In the sample analysis chip 1, the main channel 103 and the side channel 105 are disposed at positions closer to the aforementioned central point than to the plurality of wells 102. When the sample analysis chip 1 rotates, the solution in the main channel 103 moves to each of the wells 102 by the centrifugal force generated thereby.

At a one end of the main channel 103 (a first end of the main channel), a first buffer portion 110 that can accommodate a portion of the solution to be supplied to the main channel 103 is disposed. Moreover, at the other end of the main channel 103 (a second end of the main channel), a second buffer portion 111 that can accommodate a portion of the solution to be supplied to the main channel 103 is disposed. Further, on the base 101, a solution supply channel 107a of which a one end (a first end of the solution supply channel) is in communication with the first buffer portion 110 and the other end (a second end of the solution supply channel) is opened to the atmosphere, and an air vent channel 107b of which a one end (a first end of the air vent channel) is in communication with the second buffer portion 111 and the other end (a second end of the air vent channel) is opened to the atmosphere, are formed.

The main channel 103 is formed such that a ridge 103a protruding toward the central point is placed between wells 102 adjacent to each other. Herein, the "wells 102 adjacent to each other" refer to the wells that are disposed at the front and back in the channel through which the solution flows from the main channel 103 to the well 102. Moreover, the "ridge 103a protruding toward the central point" refers to a portion having a curved shape that curves maximally toward the central point. In this manner, by forming the main channel 103 such that the ridge 103a protruding toward the central point is placed between wells 102 adjacent to each other, a solution injected into the main channel 103 is naturally interrupted at the ridge 103a while the chip is rotating, hence variation of the amount of the solution dispensed to each well 102 can be reduced.

The channel width of the main channel 103 is narrow in the ridge 103a and broad in the valley 103b.

When the amount of a solution present in the area corresponding to the ridge 103a is small, variation of the amount of the dispensed solution decreases. Accordingly, the cross-sectional area of the main channel 103 in the ridge 103a is smaller than the cross-sectional area of the other portions. In order to decrease the cross-sectional area of the main channel 103 in the ridge 103a, the channel width of the ridge 103a may need to be narrowed, or the depth of the main channel 103 in the ridge 103a may need to be reduced. Alternatively, the channel width of the ridge 103a may be narrowed, and the depth of the main channel 103 in the ridge 103a may be reduced. Moreover, it is preferable for the cross-sectional area of the main channel 103 to be gradually narrowed toward the ridge 103a.

Furthermore, by adjusting the channel width of the valley 103b, the amount of a solution dispensed to each of the wells 102 can be set. In this manner, the main channel 103 positioned between two adjacent ridges 103a functions as a chamber C used to dispense a solution to a single well 102 in a predetermined volume. In the present embodiment, the chamber C composed of the main channel 103 extending from the ridge 103a to another ridge 103a adjacent thereto is coupled with each well 102 by one-to-one correspondence, and the number of the chambers C disposed is the same as the number of the wells 102. The respective chambers C have the same shape, the same size, and the same volume. Therefore, when the solution accommodated in each chamber C is dispensed to each well 102, the solution is evenly dispensed to each well 102 in the same amount.

The side channel 105 has the shape of a conduit that communicates the valley 103b of the main channel 103 with the well 102. The side channel 105 is in the form of a straight line oblique to the straight line connecting the central point to the well 102. Since the side channel 105 is oblique as described above, when a centrifugal force is applied, air in the well 102 moves toward the main channel 103 along the inside of the side channel 105 (an inside surface positioned at the central point side), and the solution moves toward the well 102 along the outside of the side channel 105 (an inside surface positioned at the well 102 side). Consequently, it is possible to smoothly move the solution into the well 102. It is preferable for the side channel 105 to be oblique such that an angle formed between the direction of the central point and the side channel 105 is between 10° and 80°. If the angle is 10° or less, the air vented from the well 102 hinders the solution from moving into the well 102 in some cases. If the angle exceeds 80°, the centrifugal force applied to the direction of the side channel 105 is weakened, hence the solution does not move to the well 102 in some cases.

The valley 103b of the main channel 103 is the site where the well 102 communicates with the main channel 103, that is, the site where the main channel 103 is connected to the side channel 105. Therefore, it is possible to inhibit the solution from remaining in the main channel 103 when the solution is dispensed. This is because the valley 103b is the site farthest away from the central point between the adjacent ridges 103a of the main channel 103.

At the stage in which the chip has not been rotated, a communication port between the main channel 103 and the well 102 has a width and cross-sectional area to such an extent that does not allow the solution to move into the well 102. The width and cross-sectional area of the communication port between the main channel 103 and the well 102 are set to be a suitable size based on the strength of surface tension of the solution. For example, when water is used as a solvent, it is preferable for the communication port to have a rectangular shape having a height of 2 mm or less and a width of 2 mm or less. Moreover, when water is used as a solvent, a cross-sectional area of the communication port is preferably 4 mm$^2$ or less.

Furthermore, the side channel 105 and the well 102 are connected to each other through a point closest to the central point in the well 102 so as to prevent air from remaining in the well 102.

The volume of the well 102 is preferably from 1 μl to 100 μl. If the volume of the well 102 is smaller than 1 μl, sufficient centrifugal force is not applied, whereby the solution is not easily provided to the well 102. Moreover, if the volume of the well 102 exceeds 100 μl, mixing properties of reagents may deteriorate, or uniformity of the internal temperature of the well 102 may deteriorate.

A position detection structure 108 is formed in the outer circumferential portion of the sample analysis chip 1. The position detection structure 108 is formed on one site of the outer circumference of the sample analysis chip 1 and configured such that a predetermined relationship is established between the position of the position detection structure 108 and the position of each well 102. For example, in the present embodiment, the position detection structure 108 is formed in the vicinity of the well 102 closest to the first buffer portion 110 in the flow direction of the solution.

The position detection structure 108 is disposed on the base 101 and is used to detect the position and angle of each well before and after centrifugation performed by using the rotation center as a center.

In the present invention, the position detection structure 108 has a portion to be mechanically detected that includes a notch, a hole, or a protrusion.

Specifically, the position detection structure 108 is a notch that is formed so that a portion of the outer circumference of the sample analysis chip 1 is cut of in a shape approximate to a rectangle.

Moreover, the position detection structure 108 may have an optical-detected portion. In this case, the surface roughness or optical characteristics of the portion to be optically detected are different from the surface roughness or optical characteristics of the site of the base 101 at which the optical-detected portion is not disposed.

Specifically, in the outer circumference of the sample analysis chip 1, the portion where the position detection structure 108 is not disposed has fine concavities and convexities formed by sand blasting, etching, emboss processing, or the like and exhibits a low optical transparency. As a result, the position of the position detection structure 108 is easily detected by detecting a degree of light scattering by using, for example, an optical sensor or a laser sensor. Furthermore, since the position of the position detection structure 108 can be detected by an optical detection mechanism, the position can be detected in a state where the mechanism does not come into contact with the sample analysis chip 1.

In addition, since the position detection structure 108 is a notch, the position thereof can be detected by a mechanical method using a contact switch, instead of an optical method using an optical sensor or a laser sensor. In this case, the mechanical method is inappropriate for detecting the position while the sample analysis chip 1 is rotating at a high speed. However, an instrument used to detect the position of the sample analysis chip 1 can be configured at a low cost.

Moreover, in the outer circumferential portion of the sample analysis chip 1, three support portions 109 are formed at intervals of 120° along a circle. The support portions 109 are dents to which an instrument for rotating the sample analysis chip 1 is latched. The instrument can hold the sample analysis chip 1 by, for example, latching claw members to the support portions 109. The shape, number, and arrangement of the support portions 109 can be set according to the configuration of the instrument. The number of the support portions 109 is not limited, as long as the support portions 109 that are adjacent to each other along the circumferential direction of the sample analysis chip 1 form an angle less than 180° based on a center which is the central point of the sample analysis chip 1. In addition, the support portions 109 may be through-holes penetrating the base 101 in the thickness direction thereof, and in this case, the sample analysis chip may have two support portions 109.

Figure 5:
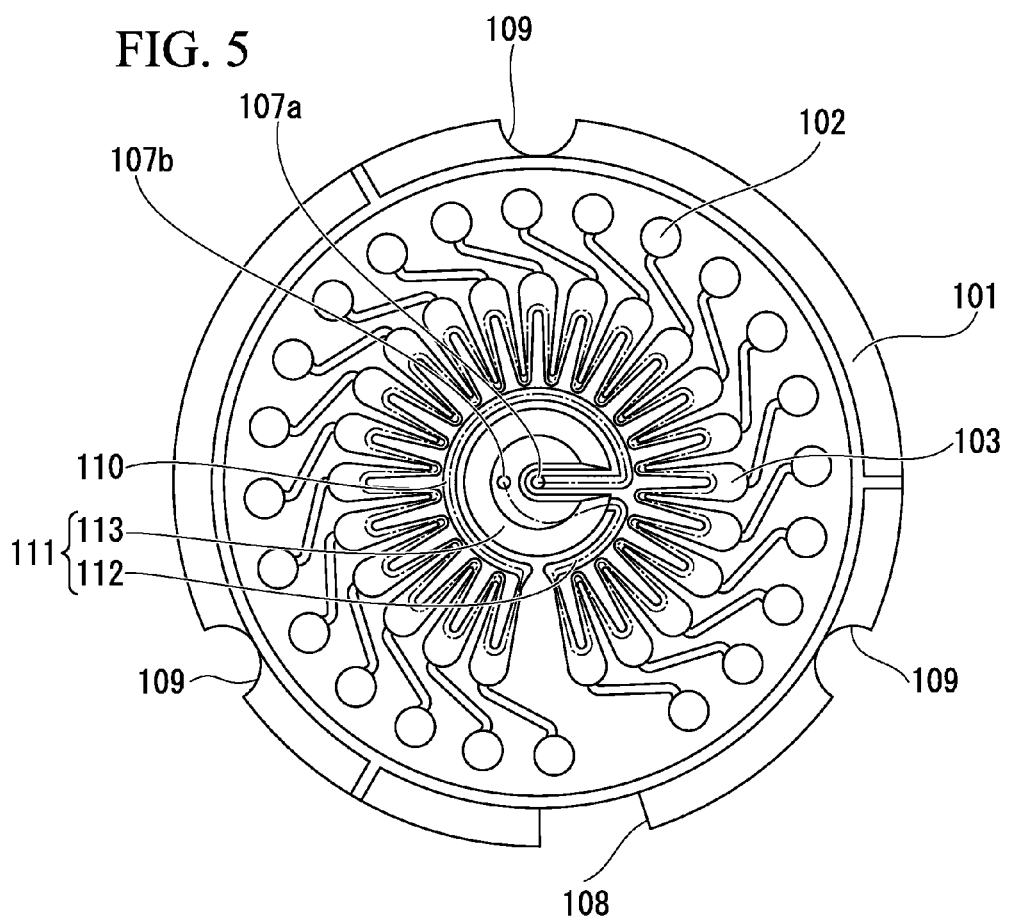
FIG. 5 is a plan view of the aforementioned sample analysis chip and shows a flow path of a solution.
Figure 6:
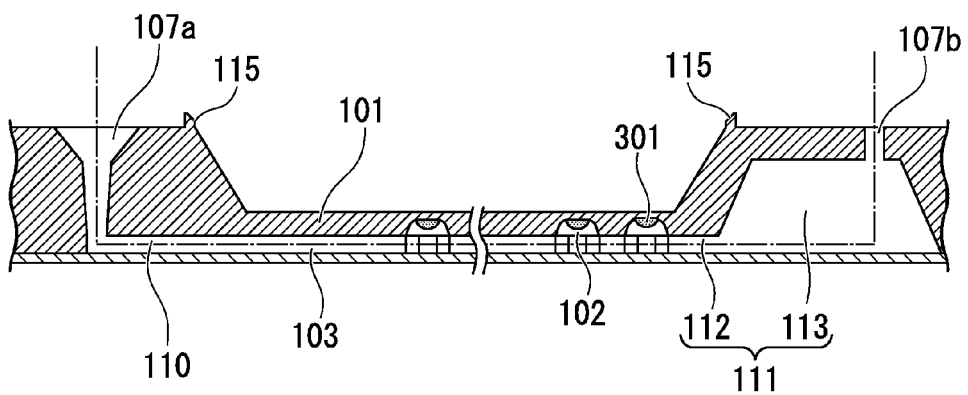
FIG. 6 is a development view obtained when the aforementioned sample analysis chip is developed along the flow path shown in FIG. 5.

FIG. 5 is a plan view of the sample analysis chip 1 and shows a flow path of the solution. FIG. 6 is a development view obtained when the sample analysis chip 1 is spread along the flow path shown in FIG. 5.

As shown in FIGS. 5 and 6, the first buffer portion 110 has a space for holding a portion of the solution between the solution supply channel 107a and the main channel 103. Similarly to the main channel 103, the first buffer portion 110 is formed on the base 101 in the form of a groove, and is shaped into a channel by being sealed by a second base 120. It is preferable for the volume of the first buffer portion 110 to be set according to the amount of expansion at the time when the solution supplied to the sample analysis chip 1 is heated. In the present embodiment, the first buffer portion 110 is formed such that it curves around the outside of a storage tank 113 in the second buffer portion 111. In the present embodiment, the cross-sectional shape of the first buffer portion 110 that is orthogonal to the flow direction of the solution is a quadrangle.

The second buffer portion 111 includes a conduit portion 112 that has the same cross-sectional shape as that of the first buffer portion 110 and the storage tank 113 that is in communication with the conduit portion 112.

A first end of the conduit portion 112 is in communication with the main channel 103, and a solution flows into the conduit portion 112 from the main channel 103. The conduit portion 112 curves around the outside of the storage tank 113. The distance between the central point of the sample analysis chip 1 and the conduit portion 112 is the same as the distance between the central point and the first buffer portion 110. As a result, when the sample analysis chip 1 rotates on the central point, the solution positioned in the conduit portion 112 and the solution positioned in the first buffer portion 110 are applied with the centrifugal force of the same magnitude.

The length of the conduit portion 112 in the flow direction of the solution may be shorter than the length of the first buffer portion 110 in the flow direction of the solution.

The storage tank 113 is formed such that in the portion where it is connected to the conduit portion 112, the cross-sectional area thereof orthogonal to the flow direction of the solution becomes greater than the cross-sectional area of the conduit portion 112. Moreover, the sum of the volume of the storage tank 113 and the volume of the conduit portion 112 is greater than the volume of the main channel 103. Inside the storage tank 113, a portion of the solution in the main channel 103 and a portion of oil which will be described later are stored. Furthermore, the height of the storage tank 113 (the height measured from a surface of the second base 120 that faces the base 101 side, in a direction perpendicular to the above surface) is greater than the height of the conduit portion 112 (the height measured from a surface of the second base 120 that faces the base 101 side, in a direction perpendicular to the above surface). Consequently, in a state where a solution (for example, a sample-containing aqueous solution) having a high specific gravity is stored in the storage tank 113, if a solution (for example, a mineral oil) having a specific gravity lower than that of the above solution flows into the storage tank 113 through the conduit portion 112, the solution having a low specific gravity moves to the surface of the solution having a high specific gravity and covers the solution having a high specific gravity.

Next, a production method of the sample analysis chip of the present invention will be described.

First, as shown in FIG. 1, molding is performed by using a molding die to form the base (the first base) 101 having the wells 102 and a channel (consisting of the main channel 103 and the side channels 105).

On a first surface of the base 101 in the thickness direction thereof, a groove-shaped structure, which becomes wells 102, the main channel 103, the side channels 105, the solution supply channel 107a, the air vent channel 107b, the first buffer portion 110, and the second buffer portion 111 of a production, is formed. Herein, the solution supply channel 107a and the air vent channel 107b are also opened to a second surface of the base 101 in the thickness direction thereof. Moreover, on the aforementioned second surface, a lip portion 115 which has the form of a continuous wall surrounding the solution supply channel 107a and the air vent channel 107b is integrally formed.

When the thickness of the base 101 is in a range of 10 μm to 300 μm, both the thermal conductivity and sealing properties of the base 101 can be preferably satisfied. If the thickness of the base 101 is greater than 300 μm, thermal capacity thereof may increase, and thermal responsiveness thereof may deteriorate.

As the material of the base 101, resins which have an optical transparency can be preferably used. Moreover, when the solution in the well 102 is subjected to optical analysis (fluorimetry, colorimetry, or the like), it is preferable for the base 101 to have a high transparency. For example, the material of the base 101 is not particularly limited as long as the material does not influence the sample. However, particularly, if resin materials containing any of polypropylene, polycarbonate, and acryl are used, excellent visible light transmittance can be secured. As polypropylene, homopolypropylene or random copolymers of polypropylene with polyethylene can be used. In addition, as acryl, polymethyl methacrylate or copolymers of methyl methacrylate with other monomers such as methacrylic acid esters, acrylic acid esters, and styrene can be used. If these resin materials are used, heat resistance or strength of the chip can be secured. Examples of materials other than the resin materials include metallic materials such as aluminum, copper, silver, nickel, brass, and gold. When the metallic materials are used, excellent thermal conductivity and sealing properties can be obtained.

If the bottom of the well 102 of the base 101 is made transparent, fluorescence or the like can be externally detected and analyzed. In the present invention, "transparent" and "optical transparency" mean that an overall average transmittance of a formed portion is 70% or higher in a visible light region (a wavelength of 350 nm to 780 nm).

When the resin material is used, various resin molding methods such as injection molding and vacuum molding, machine cutting, and the like can be used as a processing method of the base 101. When the metallic material is used, the base 101 can be formed by means of grinding processing or etching by using a thick base or by performing press processing or spinning on a thin metal sheet.

Particularly, when the resin material containing any of polypropylene, polycarbonate, and acryl is used as the base 101, excellent optical transparency, heat resistance, and strength can be secured. Moreover, when the thickness of the base 101 is in a range of 50 μm to 3 mm, excellent optical transparency, heat resistance, and strength can be secured, and concavities can be reliably processed.

Figure 3:
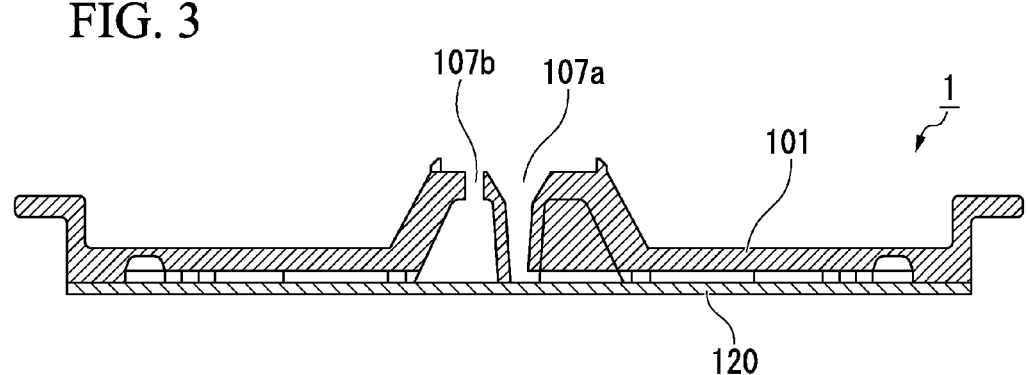
FIG. 3 is a cross-sectional view taken along the line A-A in FIG. 1.

FIG. 3 is a cross-sectional view of the sample analysis chip 1 of the present embodiment.

As shown in FIG. 3, on the base 101, the solution supply channel 107a penetrating the chip, the main channel 103 that is for causing an injected solution to flow into the chip, the side channel 105 that extends toward the outer circumferential portion of the chip and is in communication with each well, and the well 102 that is positioned in the outer circumferential portion of the chip are formed. The cross-sectional view of FIG. 3 schematically shows the path which starts from the solution supply channel 107a, passes through the well 102, and is connected to the air vent channel 107b. The shape of the main channel 103 and the side channel 105 is not limited to the structure shown in FIG. 3. In order to fill all of the wells 102 with the injected solution, the volume of the main channel 103 needs to be greater than the total volume of the respective wells 102. However, when a reagent 301, which will be described later, is immobilized in the well 102, the amount of a solution sample to be injected into the well 102 is reduced by the volume of the reagent 301. Accordingly, the volume of the channel may be reduced by the volume of the reagent 301. When a sample is detected and measured in the well 102 via the base 101 at the side of the base 101 for causing a fluorescence reaction and conducting fluorimetry, it is preferable for the concavity of the well 102 to be in the form of a flat trapezoid.

Figure 4:
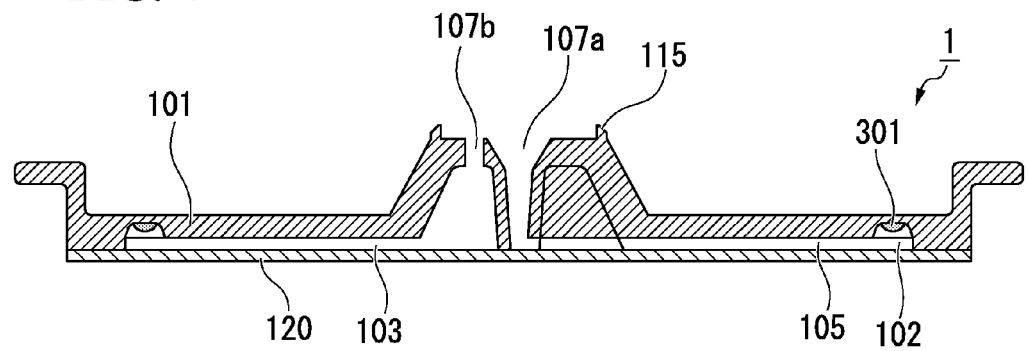
FIG. 4 is a schematic cross-sectional view of the aforementioned sample analysis chip.

FIG. 4 is a cross-sectional view of the sample analysis chip 1 of the present embodiment.

As shown in FIG. 4, after wells 102 are formed on the base 101, the reagent 301 for reaction is immobilized in the wells 102. It is possible to use different reagents for the respective wells. By immobilizing different reagents in the respective wells 102, a plurality of kinds of processing can be performed on a single specimen (sample). Moreover, a portion of the reagent for causing an actual reaction may be immobilized in the respective wells, and the remaining reagent may be introduced into the wells together with the solution sample.

Subsequently, the discoid second base 120 is bonded to the first surface of the base 101 on which the aforementioned groove-shaped structure has been formed (see FIG. 2). The second base 120 is in the form of a flat plate and functions as a lid for the groove formed on the first surface of the base 101. The second base 120 is bonded to the base 101, whereby the opening portion of the groove formed on the base 101 is sealed.

The material of the second base 120 can be appropriately selected from the materials described above as the materials of the base 101.

Examples of the method of bonding the bases to each other include a method in which a resin coating layer is disposed as an adhesive layer on one of the bases, and the resin coating layer is melted such that the two bases adhere to each other. It is preferable for the resin coating layer to be disposed on the base made of a metallic material having a high thermal conductivity and to be subjected to melt adhesion. As the material of the resin coating layer, resin materials such as polyethylene terephthalate (PET), polyacetal, polyester, and polypropylene can be used.

In the step of bonding the base 101 to the second base 120, it is preferable to use a resin material, which is easily microfabricated and has optical transparency suitable for fluorimetry, for the base 101, and to use a material, which is easily bonded to the base 101 by melt adhesion, for the second base 120. As the material of the second base 120, metallic materials which have a high thermal conductivity and include a resin coating layer for melt adhesion can be preferably used. If the resin coating layer is formed on the surface of the metallic materials, chemical resistance of the metallic materials does not need to be taken into consideration at the time of selecting materials.

When the resin coating layer is formed on the surface of the metallic material of the second base 120, if an anchor layer is formed as an underlayer of the resin coating layer, the two bases can be fused with each other by using a laser. It is preferable for carbon black absorbing light of a laser wavelength (light-absorbing material) to be kneaded into the anchor layer suitable for causing fusion by using a laser. In this case, when being irradiated with laser light, the anchor layer generates heat, whereby the melt adhesion can occur in the resin coating layer.

Moreover, carbon black may be added not to the anchor layer but to the resin coating layer, or alternatively, the surface of the resin coating layer may be painted with black. For example, the resin coating layer can also be efficiently melted by being irradiated with light of an infrared photodiode laser having a wavelength of about 900 nm. In the laser welding, the entire sample analysis chip 1 does not need to be heated as it does in thermal welding. Accordingly, it is possible to bond the base 101 to the second base 120 without exerting much influence on the sample analysis chip 1 or the reagent immobilized in the sample analysis chip 1.

Next, the action of the sample analysis chip 1 of the present embodiment will be described. FIGS. 7A, 7B, 7C, and 7D are views for illustrating the action of the sample analysis chip 1. FIGS. 8A, 8B, 8C, 8D, and 8E are plan views schematically showing how a solution moves when the sample analysis chip 1 is used. FIGS. 9A, 9B, 9C, 9D, and 9E are plan views schematically showing how the solution moves when the sample analysis chip 1 is used.

As shown in FIG. 7A and FIGS. 8A to 8D, a solution X1 is supplied from the solution supply channel 107a into the main channel 103, whereby the main channel 103 is filled with the solution. Moreover, a portion of the solution is also supplied to the first buffer portion 110 and the second buffer portion 111.

Figure 7A:
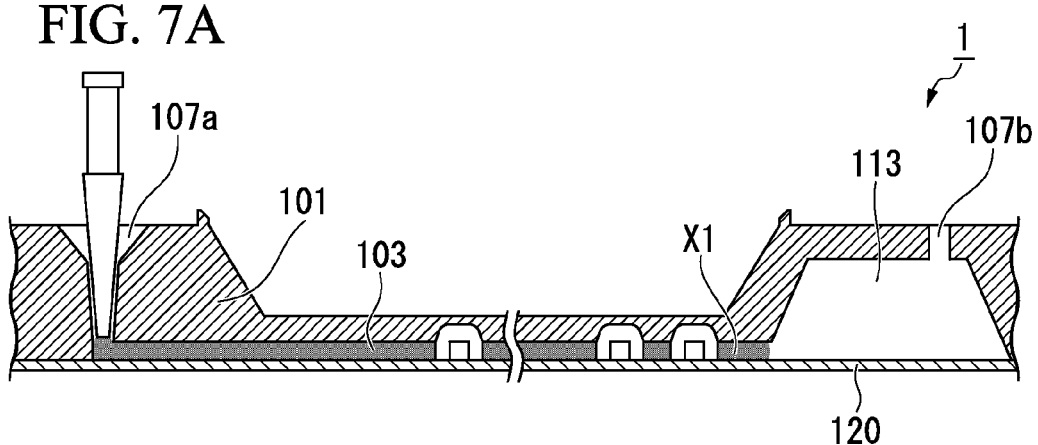
FIG. 7A is a view for illustrating the action of the aforementioned sample analysis chip.
Figure 7B:
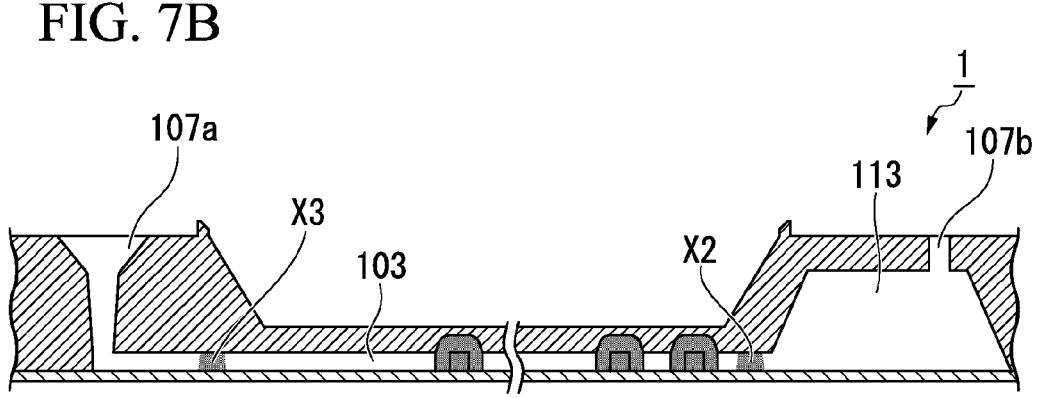
FIG. 7B is a view for illustrating the action of the aforementioned sample analysis chip.
Figure 7C:
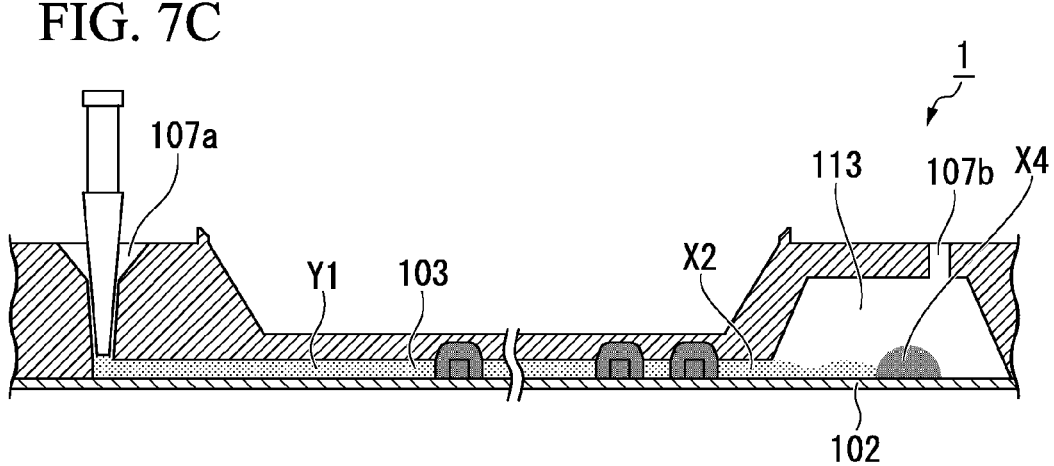
FIG. 7C is a view for illustrating the action of the aforementioned sample analysis chip.
Figure 7D:
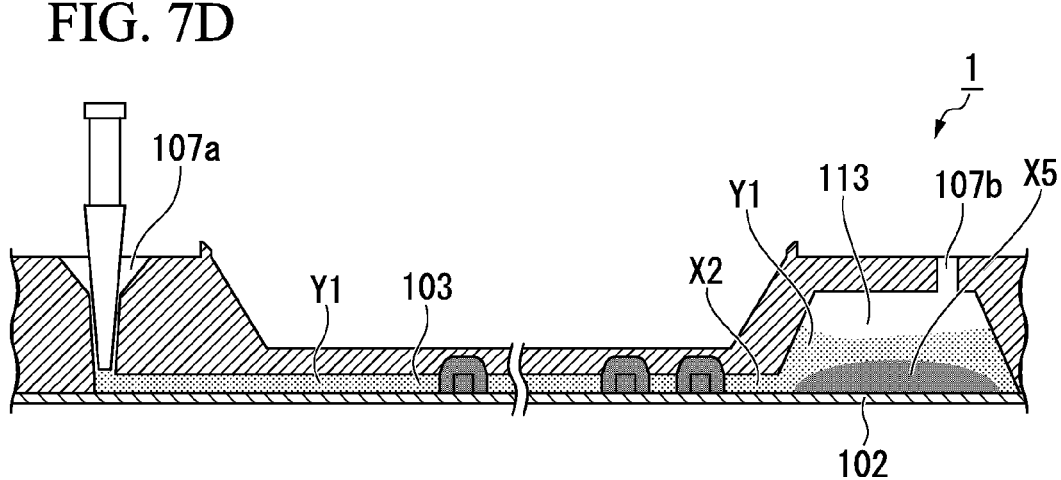
FIG. 7D is a view for illustrating the action of the aforementioned sample analysis chip.
Figure 8A:
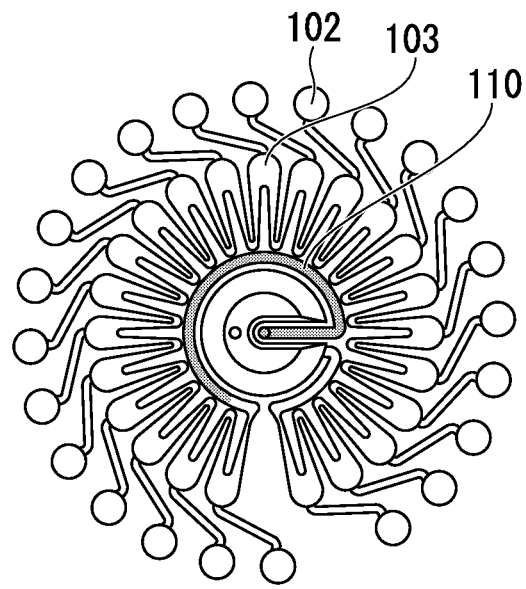
FIG. 8A is a plan view schematically showing how a solution moves when the aforementioned sample analysis chip is used.
Figure 8B:
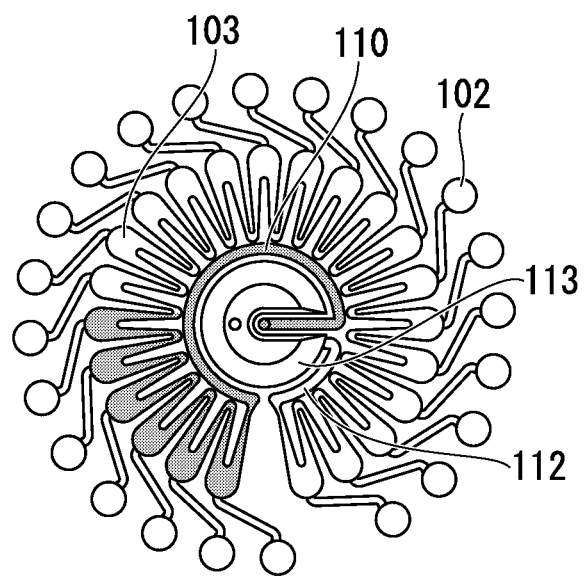
FIG. 8B is a plan view schematically showing how a solution moves when the aforementioned sample analysis chip is used.
Figure 8C:
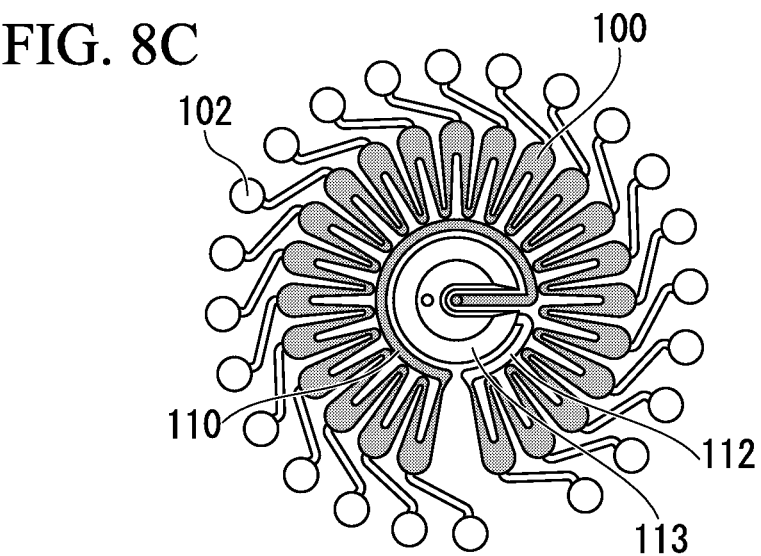
FIG. 8C is a plan view schematically showing how a solution moves when the aforementioned sample analysis chip is used.
Figure 8D:
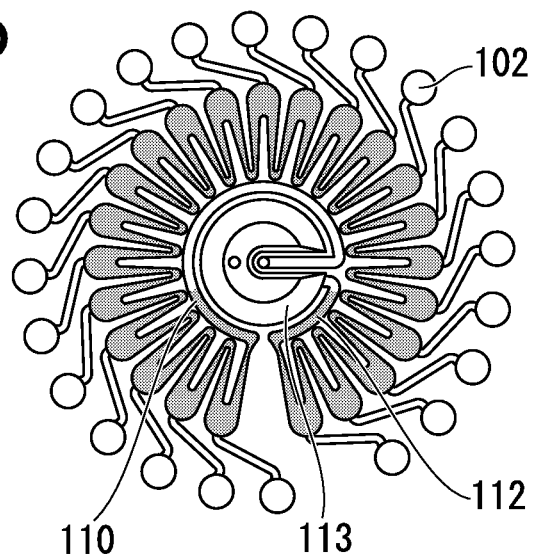
FIG. 8D is a plan view schematically showing how a solution moves when the aforementioned sample analysis chip is used.
Figure 8E:
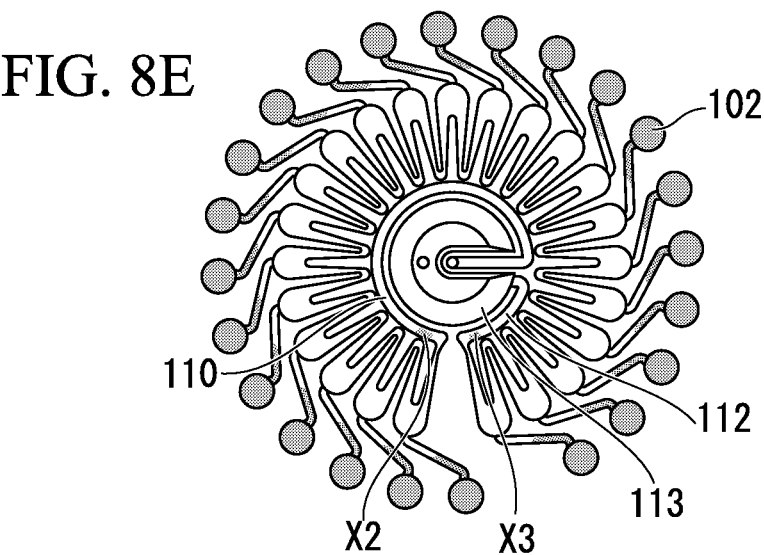
FIG. 8E is a plan view schematically showing how a solution moves when the aforementioned sample analysis chip is used.

As shown in FIGS. 7B and 8E, the sample analysis chip 1 of the present embodiment is rotated to generate a centrifugal force, and by the centrifugal force, the solution supplied into the main channel 103 is dispensed to the respective wells 102. The sample analysis chip 1 is discoid, and the respective wells 102 are concentrically arranged. Accordingly, the solution is dispensed to the respective wells 102 by the centrifugal force of the same magnitude. Furthermore, the respective wells 102 are arranged along a single circumference. Consequently, if an analysis area is set for one of the plurality of wells 102, by rotating the sample analysis chip 1 on the central point thereof as the rotation center, sequential analysis can be performed on all of the wells 102.

Herein, when the solution in the main channel 103 (chamber C) positioned between two ridges 103a moves to the wells 102 by the centrifugal force, a slight amount of the solution in another chamber C adjacent to a certain chamber C moves to the certain Chamber C. By dividing and dispensing the solution beforehand, which is in an amount corresponding to sum of the slight amount of the solution, to the first buffer portion 110 and the conduit portion 112, the shortage in the solution to be moved from the chambers C positioned at both ends of the main channel 103 to the wells 102 can be offset.

At this time, after centrifugation processing is completed, a portion of the solution (solution X2 or X3) remains in the first buffer portion 110 and the conduit portion 112 in some cases (see FIGS. 7B and 8E). If the solution remaining after the completion of centrifugation processing then flows into the well 102, it may exert an influence on the accuracy of analysis in the well 102. Therefore, an operation for pushing out the solution remaining in the first buffer portion 110 and the conduit portion 112 to the storage tank 113 is performed.

As shown in FIGS. 7C, 9A, 9B, and 9C, in order to push out the solution remaining in the first buffer portion 110 and the conduit portion 112 to the storage tank 113, a solution Y1 that does not exert an influence on the reaction in the well 102 is supplied from the solution supply channel 107a into the main channel 103. As the solution that does not exert an influence on the reaction in the well 102, for example, a mineral oil is preferable when a PCR reaction is performed in the well 102.

Figure 9A:
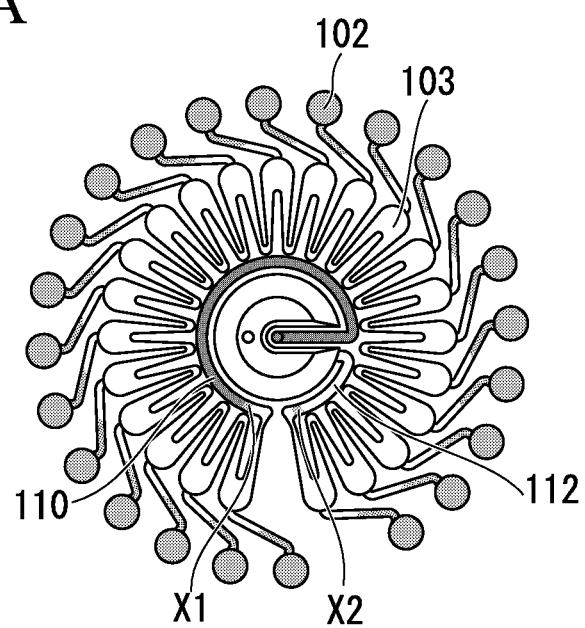
FIG. 9A is a plan view schematically showing how a solution moves when the aforementioned sample analysis chip is used.
Figure 9B:
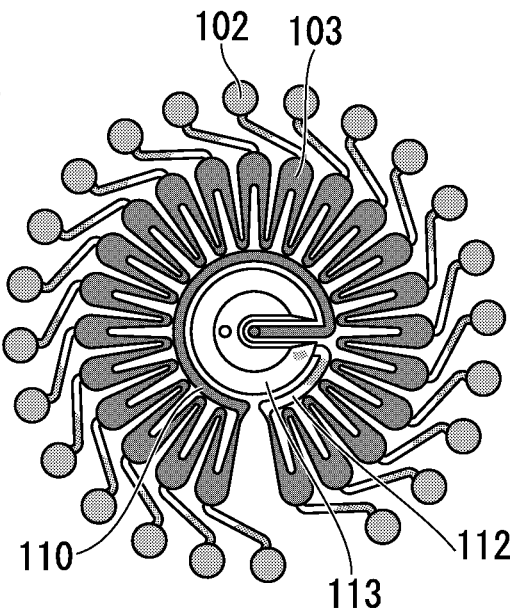
FIG. 9B is a plan view schematically showing how a solution moves when the aforementioned sample analysis chip is used.
Figure 9C:
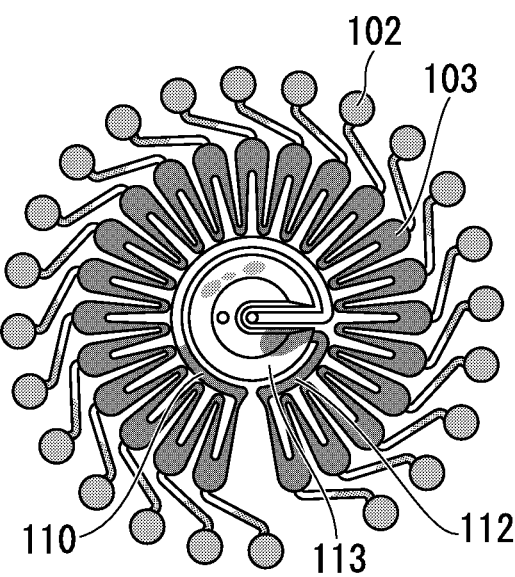
FIG. 9C is a plan view schematically showing how a solution moves when the aforementioned sample analysis chip is used.
Figure 9D:
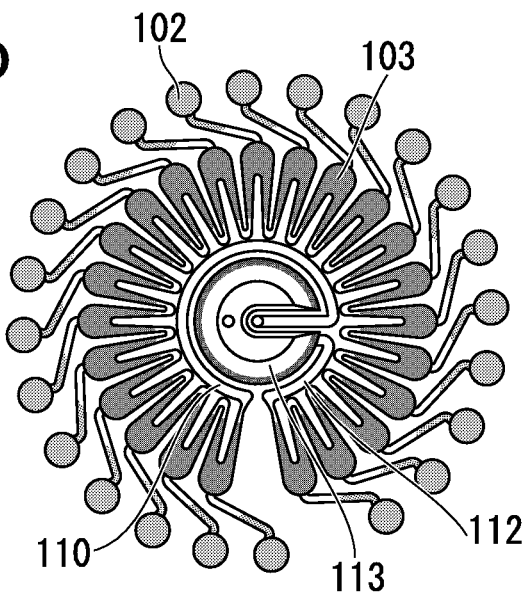
FIG. 9D is a plan view schematically showing how a solution moves when the aforementioned sample analysis chip is used.
Figure 9E:
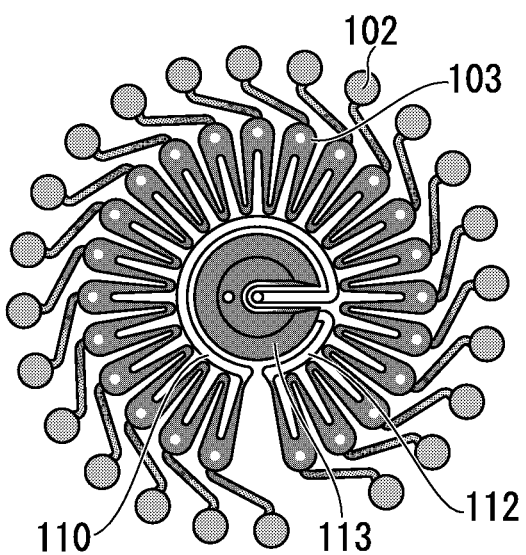
FIG. 9E is a plan view schematically showing how a solution moves when the aforementioned sample analysis chip is used.

As shown in FIG. 9D, after the solution remaining in the first buffer portion 110 and the conduit portion 112 is pushed out to the storage tank 113, even if the sample analysis chip 1 is rotated, the solution in the storage tank 113 is merely pushed against the inner wall of the storage tank 113 or the conduit portion 112 and does not flow back to the main channel 103. Even after the centrifugation processing is completed, as shown in FIG. 9E, the main channel 103 has no space to which the solution having been pushed out into the storage tank 113 can return, and the main channel 103 is filled with a solution such as the aforementioned mineral oil.

As a result, it is possible to minimize the influence that is exerted on the reaction in the well 102 by the solution remaining in the first buffer portion 110 and the conduit portion 112.

Next, the sample analysis method according to an embodiment of the present invention will be described by exemplifying a case where the sample analysis chip 1 of the present embodiment is used.

The sample analysis chip 1 can be used for detecting or analyzing biochemical substances by using sample solutions containing, for example, DNA or proteins. In the respective wells 102, the sample solutions or reagents can be immobilized. The operation to immobilize the sample solutions or reagents in the respective wells 102 is performed at the time of producing the sample analysis chip 1. If the reagents are immobilized in the respective wells 102, and a solution sample is dispensed to the respective wells 102, different reagents can be used for the respective wells 102. Moreover, if samples are immobilized in the respective wells 102, and a liquid reagent is dispensed to the respective wells 102, different samples can be used for the respective wells 102.

Hereinafter, an example of performing SNPs analysis by using a DNA-containing sample will be described.

For example, different SNPs probes and enzymes are immobilized in the respective wells 102. By doing this, reactions for identifying various types of SNPs can be simultaneously performed in a single sample analysis chip 1.

Specifically, different types of SNPs are dropped to the wells 102 of the base 101 by using a pipette, the base 101 is subjected to centrifugation for about 10 minutes at 2,000 rpm to 3,000 rpm by using a centrifugal device, and the SNPs are dried in the state where the solution surface thereof is flat. In this manner, the SNPs can be immobilized in the wells. Thereafter, the base 101 is bonded to the second base 120.

Subsequently, a solution such as a reagent is injected into the main channel 103 from the solution supply channel 107a. At this stage, only the main channel 103 is filled with the solution, and the solution does not flow into the side channel 105 as described above. This is because the surface tension of the solution acts, and pneumatic pressure is applied from the side of wells since there is no air vent hole at the side of the well 102. In addition, the operation for injecting the solution into the main channel 103 may be performed manually or may be automatically controlled by a dispensing robot.

Thereafter, the sample analysis chip 1 is rotated on the central point thereof as the rotation center at a predetermined rotation speed. At this time, as a device for rotating the sample analysis chip 1, for example, it is possible to use a low-speed centrifuge having a rotation speed of 1,000 rpm to 3,000 rpm. It is also possible to use a centrifuge having a rotation speed exceeding 3,000 rpm.

Moreover, as the device for rotating the sample analysis chip 1, it is possible to use a device provided with claws corresponding to the position and shape of the support portion 109 of the sample analysis chip 1 of the present embodiment. In this case, the sample analysis chip 1 can be stably rotated.

By the device for rotating the sample analysis chip 1, the sample analysis chip 1 is caused to rotate on a rotation axis which passes through the central point of the sample analysis chip 1 and extends in the vertical direction of the sample analysis chip 1 (in the present embodiment, the thickness direction of the second base 120). The rotation speed needs to be such a speed that makes the centrifugal force applied to the solution greater than the aforementioned pneumatic pressure and the surface tension and causes the solution to flow into the wells 102. The rotation speed is preferably about 1,000 rpm or higher, though the speed also depends on the form of the chip. If the rotation speed of the chip is lower than about 1,000 rpm, the solution does not flow into some of the wells 102 in some cases, hence variation may occur in the amount of the solution.

After the sample solution is dispensed by centrifugation, in order to prevent mixing or contamination of the solution in the respective wells 102, the oil (mineral oil) that does not hinder the reaction of the sample and the reagent is dispensed to the respective wells by the same step. As the oil, an oil that has a specific gravity lower than that of the solution dispensed as above needs to be used. This is because the oil needs to play a role of stopper of the respective wells 102 at the side of the side channel 105, when the solution has been dispensed by the centrifugal force due to the rotation of the sample analysis chip 1. If the specific gravity of the oil is lower than that of the solution dispensed beforehand, when the sample analysis chip 1 is rotated, the oil is positioned at the side closer to the rotation center, and the solution dispensed beforehand stays at the side farther from the rotation center.

In the well 102, the reagent and the sample are mixed with each other. Thereafter, for example, the solution in the well 102 is heated to denature DNA, and the solution in the well 102 is cooled such that the DNA is bonded to the SNPs probe. At this time, the lip portion 115 undergoes deformation such as crushing by a jig or the like not shown in the drawing. As a result, the solution supply channel 107a and the air vent channel 107b are sealed by the jig, whereby it is possible to prevent the phenomenon in which the solution overflows in a case where the volume of the solution expands or bubbles generate when the sample analysis chip 1 is heated.

Moreover, in the present example, when the volume of the solution expands in the sample analysis chip 1 due to heating, the solution whose volume expands and thus overflows from the main channel 103 is stored in the first buffer portion 110 and the second buffer portion 111. Accordingly, it is possible to prevent the solution from overflowing from the solution supply channel 107a and the air vent channel 107b.

After the DNA is bonded to the SNPs probe in the well 102, the reaction state of the solution in the well 102 can be analyzed by a technique such as fluorescence detection. A device performing the fluorescence detection or the like can detect the position of the well 102 that should be measured among the plurality of wells 102, by means of detecting the position detection structure 108, which is disposed in the outer circumferential portion of the sample analysis chip 1, by using a photosensor or a laser sensor. The device can measure the reaction state of the solution in the predetermined well 102 by rotating the sample analysis chip 1.

By including the mechanisms that act on the sample analysis chip in each step as described above, the sample analysis chip can save space and make a sample analysis easy.

It is also possible to perform a PCR reaction in the well 102 of the sample analysis chip 1. In this case, the PCR reaction is performed by using a heating-cooling device not shown in the drawing that comes into contact with the base 101 and the second base 120. Moreover, when the base 101 is made of an optically transparent resin material, and the second base 120 is made of a metal plate, the temperature of the solution in the well 102 is controlled mainly through the second base 120.

Next, a sample analysis method will be described in detail by using specific examples of the sample analysis method of the present embodiment.

An example of gene analysis includes detection of K-ras gene mutation or germline mutation. Regarding the K-ras gene mutation, the identification method thereof is desired to be established for cancer treatment, and identification of germline mutation is considered to be able to be used to estimate medicinal effect and the like.

Detection of Germline Mutation

The germline mutation can be detected by identifying SNPs. As one of the identification methods of SNPs, for example, PCR-Preferential Homoduplex Formation Assay (PCR-PHFA) utilizing fluorescence is used. According to this method, the mutation is detected by the difference in a degree of luminescence between fluorescent reagents. If the sample analysis chip of the present invention is used, a sample can be accurately analyzed since the amount of the solution dispensed to the respective wells shows a small degree of variation. Accordingly, the sample analysis chip of the present invention is suitable for SNPs detection. Moreover, the sample analysis chip can also be used for SNPs detection methods other than the above, such as Invader (registered trade mark) assay.

A nucleic acid of a specimen obtained from blood or the like is purified to prepare a solution sample. The nucleic acid of the specimen is amplified before the solution sample is injected into the sample analysis chip 1 of the present embodiment, or after the solution sample is injected into the sample analysis chip 1 and before the solution is dispensed. For example, multiplex PCR is performed by using VKORC1, CYP2C9*3, CYP2C9*2, and a positive control so as to amplify gene fragments in the sample. The PCR is performed by providing the sample solution.

In the detection method described above, two wells 102 are necessary to identify a single SNP. Accordingly, it is preferable to use the sample analysis chip 1 in which 10 or more wells 102 are formed for a single specimen sample. In the respective wells 102, a reagent for detecting SNP is immobilized.

The solution of the sample having undergone nucleic acid amplification by PCR as described above is dispensed to the respective wells 102. The temperature of the respective wells 102 is controlled, and mutation is detected by the difference in a degree of luminescence between fluorescent reagents mixed into the reagent for detecting SNP in the wells 102. If only one of the two wells 102 tests positive for a single SNP, the sample can be identified to be homogeneous, and if both the wells 102 test positive for a single SNP, the sample can be identified to be heterogeneous.

Detection of K-Ras Gene Mutation

In the present example, a sample analysis chip 1 that is different from the sample analysis chip 1 used for detection of germline mutation described above is used.

In the wells 102 for detecting the above gene mutation, a nucleic acid probe-containing reagent is immobilized. Moreover, the nucleic acid probe-containing reagent contains a fluorescent reagent. There are wild-type K-ras gene and thirteen types of mutations thereof. Accordingly, in order to detect K-ras genes, it is preferable to use the sample analysis chip 1 in which at least fourteen wells 102 are formed. Moreover, it is preferable that reagents corresponding to the respective wells 102 are immobilized in the wells.

Cancer cells such as colorectal cancer cells are collected, and the nucleic acid of the specimen is purified to prepare solution sample. Before the solution is injected into the sample analysis chip 1 of the present invention or before the solution is dispensed after being injected into the sample analysis chip 1, the nucleic acid of the specimen is amplified. The PCR is performed by providing the sample solution.

The solution of the sample having undergone nucleic acid amplification by the PCR as described above is dispensed to the respective wells 102.

The temperature of the wells 102 is controlled, whereby mutation can be detected by the difference in a degree of luminescence between fluorescent reagents mixed into the nucleic acid probe-containing reagent.

EXAMPLES

Hereinafter, examples of the present invention will be described, but the present invention is not limited thereto.

Example 1

SNPs Analysis Chip

In the present example, the sample analysis chip 1 is used as an SNPs analysis chip for analyzing SNPs.

As the base 101 of the SNPs analysis chip, a polypropylene (hereinafter, abbreviated to "PP")-molded article is used. This base 101 is discoid in shape as shown in FIG. 2 and has the wavy main channel 103 that is concentrically disposed, the side channels 105 having communication ports in the valleys 103b, and wells 102 that are at the end of the side channels 105. On the base 101, twenty three wells 102 and side channels 105 are formed respectively. Moreover, the area of the main channel 103 periodically changes, and the volume of the main channel between ridges 103a adjacent to each other is 12 µl.

As the second base 120 to be bonded to the base 101 made of polypropylene, a base made of aluminum sheet coated with a polypropylene resin as a resin coating layer was used. The thickness of the resin coating layer was about 0.07 mm. The melting point of the resin coating layer is around 120° C., and the resin coating layer is formed by coating the aluminum base with the resin such that the layer is melted when the aluminum side is heated.

Moreover, an anchor layer into which carbon has been kneaded is disposed between the aluminum layer and the polypropylene resin layer, such that the polypropylene layer is also melted by heat generated by laser light irradiation. In the wells 102 on the base 101 made of polypropylene, SNPs probe reagents shown in the following Table 1 describing the type of reagents were immobilized. To the other wells 102, enzymes for causing PCR reactions and enzymes for Invader reaction (see Table 1) used for fluorescence detection of SNPs were dropped by using a pipette and immobilized by drying.

TABLE 1

| Type of reagent | Amount/well (µl) |
| --- | --- |
| Probe reagent for Invader reaction | 1.28 |
| DNA polymerase, Cleavase | 1.41 |
| Buffer solution (MgCl$_2$, NaCl) Purified genome (5 ng/ul) | 12 in total |
| Mineral oil | 12 |

The base 101 made of polypropylene was superposed on the second base 120 made of aluminum, and the side of the second base 120 was heated to 130° C. or a higher temperature so as to melt the resin layer that is coated on the second base 120, whereby the base 101 made of polypropylene was welded to the second base 120 made of aluminum.

A solution sample, which was obtained by mixing the buffer solution with the purified genome described in Table 1, was provided to the SNPs analysis chip prepared by the step described above by using a pipette so as to fill the main channel 103 with the solution. At this stage, the samples had not flowed into the wells 102 and the side channels 105.

As means for applying a centrifugal force to the SNPs analysis chip, a simple centrifugal device utilizing a desktop centrifuge which is used for isolation or the like of reagents in chemical and biological reactions was prepared and used. The rotation frequency at the time of centrifugation was measured and adjusted by using a rotation frequency measuring instrument. The aforementioned simple centrifugal device is a centrifuge having claws engaged with the support portion 109. As a result of performing centrifugation at 5,000 rpm by using the centrifuge, 11 μl of the sample was sent to each of the wells 102.

Regarding the rotation direction of the SNPs analysis chip at the time of centrifugation, it was confirmed that even if the chip is rotated in any direction relative to the inclination direction of the side channel, while the rotation frequency is increasing, the behavior of the solution in the SNPs analysis chip is influenced by the rotation direction, but the rotation direction does not exert an influence and causes variation in the amount of the solution dispensed in the wells.

Thereafter, the mineral oil described in Table 1 that does not hinder the reaction was provided to the chip in the same manner as above. As a result, the wells 102 were filled with the sample, about half of the side channels 105 were filled with the remaining solution, and the other half of the channels 105 and 80% of the valleys 103b were filled with the oil.

In the present example, the probe for Invader reaction was immobilized as a reagent for reaction in twenty two wells 102. Moreover, in order to judge whether or not the reaction occurred successfully, one well was set as a negative control to confirm whether the sample was contaminated. In this manner, a reaction test was conducted on a single chip.

The reaction was alternatively performed at 95° C. and 68° C. for 35 cycles on the SNPs analysis chip which was in a state where the wells 102 were separated from one another by the oil, whereby the genome of the sample was amplified by a PCR reaction. Thereafter, the temperature was controlled to be 63° C. for 30 minutes such that a reaction used to detect fluorescence was performed in the wells 102 by an enzyme reaction.

At this time, the lip portion 115 is crushed from the top thereof by using a device not shown in the drawing. In this manner, the solution or oil in the SNPs analysis chip could be prevented from overflowing to the outside due to volume expansion caused by heating.

Furthermore, at this time, since the side of the polypropylene base (base 101) of the SNPs analysis chip was transparent, fluorescence was detected from the outside through the polypropylene base. In the present example, the fluorescence reaction was measured by a fluorescence detection device as a combination of a photomultiplier tube and optical fiber.

Figure 10:
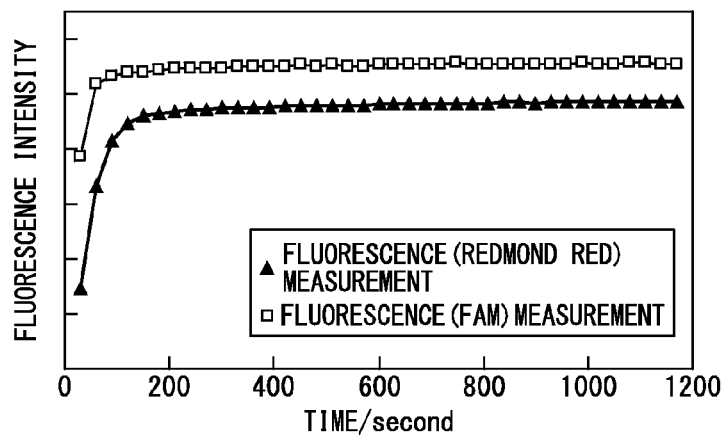
FIG. 10 is a graph showing analysis results in an example of the present invention.
Figure 11:
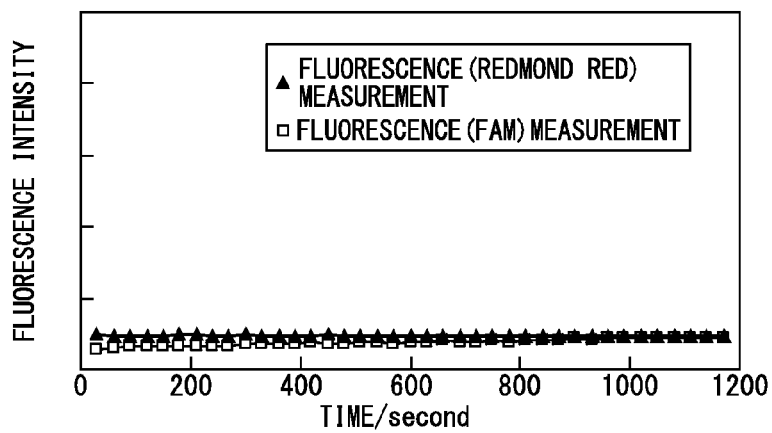
FIG. 11 is a graph showing the analysis results in an example of the present invention.
Figure 12:
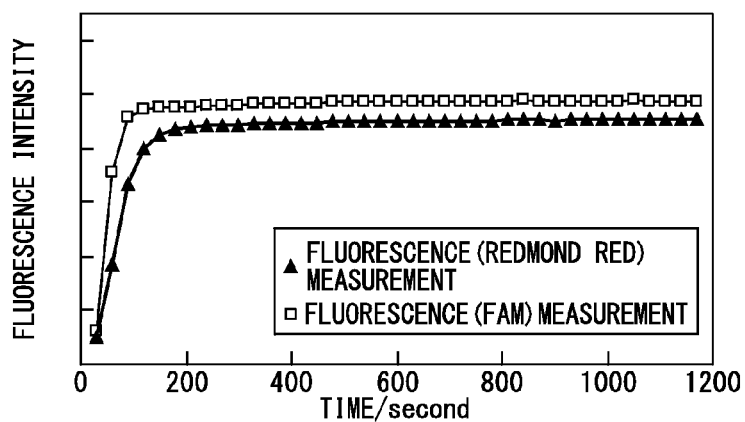
FIG. 12 is a graph showing the analysis results in an example of the present invention.

FIGS. 10 to 12 are graphs showing SNPs analysis results obtained by the fluorescence reaction detected by the present example. The ordinate of the respective graphs is the intensity of light detected and indicates fluorescence intensity, and the abscissa is a time axis.

FIG. 10 shows results obtained from a single well 102 in which the reaction occurred. From the results, it was confirmed that the reaction used to detect fluorescence occurred within a predetermined time by the mixed reagents.

FIG. 11 shows wells in which the reagents were not immobilized in advance. Accordingly, the fluorescence reaction was not detected in the wells. From this result, it was confirmed that contamination is not caused in adjacent wells.

FIG. 12 shows detection data obtained when the reagents were mixed with the sample at an optimal quantitative ratio by a general technique by using a polypropylene tube (positive control).

Comparing FIG. 10 with FIG. 12, the reaction of FIG. 10 that was performed in the chip by the present example is identical to the reaction of FIG. 12. Accordingly, it can be confirmed that the reaction of the present example is performed by an optimal quantitative ratio. Therefore, it is understood that the sample can be dispensed in a desired amount to the wells.

As in the present Example 1, in the present invention, materials suitable for the reaction were selected as the bases to be bonded to each other, and this made it possible to more simply perform the reaction in a short time and with excellent efficiency.

So far, the embodiments of the present invention have been described in detail by using an example with reference to the drawings. However, specific configuration of the present invention is not limited to the embodiments and also includes change of design and the like within a range that does not depart from the scope of the present invention.

For example, all of the wells 102 are not necessarily arranged along a single circumference. For example, for the purpose of varying the centrifugal force applied to the solution supplied to the wells 102, the distance between the rotation center and the wells 102 in the sample analysis chip 1 may be varied.

Moreover, the sample analysis chip 1 may be in the form other than the form of a disk, as long as the chip sustains weight balance while rotating.

In addition, in the main channel 103, a first side of the ridge 103a and a second side thereof that interpose the peak of the ridge 103a therebetween may be asymmetric. That is, the main channel 103 positioned at both sides of the ridge 103a may be asymmetric.

INDUSTRIAL APPLICABILITY

The reaction chip of the present invention can be used for, for example, detecting or analyzing biochemical substances in samples such as nucleic acids. Particularly, since the chip makes it possible to detect mutation of SNP, the chip can be used for techniques which detect genetic mutation such as cancer genes and genetic mutation of germ cells or somatic genes. Moreover, the chip can also be used as a container for mixing a plurality of solutions and as a reaction container.

What is claimed is:

1. A sample analysis chip comprising:
a base;
a plurality of wells that are disposed on the base; and
a channel that is disposed on the base and is connected to the plurality of wells, the channel comprising
a main channel portion that is disposed at a position closer to a rotation center than the plurality of wells on the base and is supplied with a solution which is to be dispensed to each of the plurality of wells, the main channel portion having ridges positioned near the rotation center of the base and valleys positioned near the wells relative to the ridges, the main channel portion configured to meander, and the wells being in communication with the valleys,
a first buffer portion that is in communication with a first end of the main channel portion and is capable of accommodating a portion of the solution,
a second buffer portion that is in communication with a second end of the main channel portion and is capable of accommodating a portion of the solution,
a solution supply channel having a first end of which is in communication with the first buffer portion and a second end of which is opened to the atmosphere, and
an air vent channel having a first end of which is in communication with the second buffer portion and a second end of which is opened to the atmosphere.

2. The sample analysis chip according to claim 1, further comprising
a sealing member that is fixed to the base and sealing the channels, wherein the channel is formed in a groove shape on the base.

3. The sample analysis chip according to claim 2, wherein the base has a first surface on which the channel is formed, and a second surface opposite to the first surface, and both of the second end of the solution supply channel and the second end of the air vent channel are opened to the atmosphere on the second surface.

4. The sample analysis chip according to claim 1, wherein a cross-section area orthogonal to a flow direction of the solution in the second buffer portion is greater than a cross-section area orthogonal to a flow direction of the solution in the main channel portion.

5. The sample analysis chip according to claim 1, wherein a volume of the second buffer portion is greater than a volume of the main channel portion.

6. The sample analysis chip according to claim 1, wherein a volume of the second buffer portion is greater than a volume of the first buffer portion, and
a total volume of the first buffer portion and the volume of the second buffer portion is greater than a volume of the main channel portion.

7. The sample analysis chip according to claim 1, further comprising
a lip portion which is formed in a wall shape that surrounds the second end of the solution supply channel and the second end of the air vent channel, is deformed by a device or a jig which is used to block the second end of the solution supply channel and the second end of the air vent channel, after the solution is injected into the channel, the lip portion thereby being capable of keeping the channel sealed.

8. The sample analysis chip according to claim 1, wherein the main channel portion is relatively narrow in the ridges and is relatively wide in the valleys.

9. The sample analysis chip according to claim 1, wherein the base is discoid, and the plurality of wells are disposed on a concentric circle with the base.

10. The sample analysis chip according to claim 1, further comprising
a plurality of side channels that communicate the main channel portion to the plurality of wells.

11. The sample analysis chip according to claim 10, wherein
each of the plurality of side channels is formed to become oblique to a straight line that connects the well which is connected to the side channel, among the plurality of wells, to the rotation center of the base.

12. The sample analysis chip according to claim 1, wherein
a support portion which is used to rotate the base to provide the solution by a centrifugal force is disposed on the base.

13. The sample analysis chip according to claim 12, wherein
the support portion is placed at the outer circumferential portion of the base.

14. The sample analysis chip according to claim 1, further comprising
a position detection structure which is disposed on the base and is used to detect a position and an angle of each well before and after a centrifugation process performed by using the rotation center as a center, wherein
the position detection structure has a mechanical-detected portion that consists of a notch, a hole, or a bump.

15. The sample analysis chip according to claim 1, further comprising
a position detection structure which is disposed on the base and is used to detect the position and angle of each well before and after centrifugation performed by using the rotation center as a center, wherein
the position detection structure has an optical-detected portion, and surface roughness or optical characteristics of the optical-detected portion are different from surface roughness or optical characteristics of sites of the base, at which the optical-detected portion is not provided.

16. The sample analysis chip according to claim 1, wherein
the main channel portion positioned at both sides of the ridge is asymmetrically formed.

17. The sample analysis chip according to claim 1, wherein
the base is a first base on which the plurality of wells and the channel is formed, and
the sample analysis chip further comprises a second base which is bonded to the first base.

18. The sample analysis chip according to claim 17, wherein
at least one of the first and the second bases is formed of an optically transparent material.

19. The sample analysis chip according to claim 17, wherein
the first base is formed of an optically transparent resin material, and
the second base is formed of a metallic material.

20. The sample analysis chip according to claim 1, wherein
the base rotates on the rotation center, and thus the solution in the main channel portion moves into the wells.

21. A sample analysis chip comprising:
a base;
a plurality of wells that are disposed on the base;
a channel that is disposed on the base and is connected to the plurality of wells, the channel comprising
a main channel portion that is disposed at a position closer to a rotation center than the plurality of wells on the base and is supplied with a solution which is to be dispensed to each of the plurality of wells,
a first buffer portion that is in communication with a first end of the main channel portion and is capable of accommodating a portion of the solution,
a second buffer portion that is in communication with a second end of the main channel portion and is capable of accommodating a portion of the solution,
a solution supply channel having a first end of which is in communication with the first buffer portion and a second end of which is opened to the atmosphere, and
an air vent channel having a first end of which is in communication with the second buffer portion and a second end of which is opened to the atmosphere; and
a position detection structure which is disposed on the base and is used to detect a position and an angle of each well before and after a centrifugation process performed by using the rotation center as a center, wherein the position detection structure has a mechanical-detected portion that consists of a notch, a hole, or a bump.

22. A sample analysis chip comprising:
a base;
a plurality of wells that are disposed on the base;
a channel that is disposed on the base and is connected to the plurality of wells, the channel comprising
   a main channel portion that is disposed at a position closer to a rotation center than the plurality of wells on the base and is supplied with a solution which is to be dispensed to each of the plurality of wells,
   a first buffer portion that is in communication with a first end of the main channel portion and is capable of accommodating a portion of the solution,
   a second buffer portion that is in communication with a second end of the main channel portion and is capable of accommodating a portion of the solution,
   a solution supply channel having a first end of which is in communication with the first buffer portion and a second end of which is opened to the atmosphere, and
   an air vent channel having a first end of which is in communication with the second buffer portion and a second end of which is opened to the atmosphere; and
a position detection structure which is disposed on the base and is used to detect the position and angle of each well before and after centrifugation performed by using the rotation center as a center, wherein
the position detection structure has an optical-detected portion, and
surface roughness or optical characteristics of the optical-detected portion are different from surface roughness or optical characteristics of sites of the base, at which the optical-detected portion is not provided.

23. A method of using the sample analysis chip according to claim 1 to perform sample analysis, the method comprising:
   injecting a sample solution into the main channel portion; and
   dispensing the sample solution to each of the plurality of wells by rotating the base.

24. The method of using the sample analysis chip according to claim 23, further comprising
   after dispensing the sample solution to the wells, dispensing a mineral oil to each of the wells.

25. The method according to claim 23, the method being a gene analysis method.

* * * * *